United States Patent
Redko et al.

(10) Patent No.: US 7,498,432 B2
(45) Date of Patent: Mar. 3, 2009

(54) METHOD OF SYNTHESIS OF 1, 4, 7, 10, 13, 16, 21, 24-OCTAAZABICYCLO [8.8.8] HEXACOSANE (1) AND 1, 4, 7, 10, 13, 16, 21, 24-OCTAAZABICYCLO [8.8.8] HEXACOSA, 4, 6, 13, 15, 21, 23-HEXAENE (2)

(75) Inventors: Mikhail Redko, East Lansing, MI (US); James E. Jackson, Haslett, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 394 days.

(21) Appl. No.: 10/866,858

(22) Filed: Jun. 14, 2004

(65) Prior Publication Data

US 2004/0267009 A1  Dec. 30, 2004

Related U.S. Application Data

(60) Provisional application No. 60/482,355, filed on Jun. 25, 2003.

(51) Int. Cl.
*C07D 487/00* (2006.01)
(52) U.S. Cl. .................................................... 540/472
(58) Field of Classification Search .................. 540/472
See application file for complete search history.

(56) References Cited

U.S. PATENT DOCUMENTS 4,257,955 A   3/1981  Gansow et al. .............. 540/465
4,888,032 A  12/1989  Busch ............................ 95/44
5,492,879 A   2/1996  Dye et al. .................... 502/326

FOREIGN PATENT DOCUMENTS

WO       WO 97/49691       12/1997

OTHER PUBLICATIONS

Kim, J., et al., J. Am. Chem. Soc., 121 10666-10667(1999).
Xie, Q., et al., J. Am. Chem. Soc. 122 6971-6978(2000).
Redko, M.Y., et al., JACS 125 2259-2263(2003).
Smith, P.H., et al., J. Org. Chem. 58 7939-7941 (1993).
Chassonnery,D., et al., Bull. Soc. Chim. Fr., 131(2), 188 (1994).
Ferruti, P., et al., J. Chem. Soc. (C) 2512 (1970).
Willer, R.L., et al., J. Org. Chem. 50 2368 (1985).

*Primary Examiner*—Brenda L Coleman
(74) *Attorney, Agent, or Firm*—Ian C. McLeod

(57) ABSTRACT

A process for producing compound 1,4,7,10,13,16,21,24-octaazabicyclo[8.8.8]hexacosa, 4,6,13,15,21,23-hexaene (2) and then compound 1,4,7,10,13,16,21,24-octaazabicyclo [8.8.8]hexacosane (1) from compound (2) is described. The process uses a reaction between triaminoethylamine and glyoxal in the presence of water, alcohol and tertiary amine at low temperature to produce compound 2. Then compound 1 is produced from compound 2 by reduction with an alkali metal containing ammonia as the reductant. The compounds are aza cryptands which are used to bind metals and the like for electrides, and in alkalides, medicine and water treatment, for instance.

31 Claims, 2 Drawing Sheets a) CHO-CHO, i-PrOH, -78 °C to RT
b) Na-NH$_3$, i-PrOH, -78 °C to RT

METHOD OF SYNTHESIS OF 1, 4, 7, 10, 13, 16, 21, 24-OCTAAZABICYCLO [8.8.8] HEXACOSANE (1) AND 1, 4, 7, 10, 13, 16, 21, 24-OCTAAZABICYCLO [8.8.8] HEXACOSA, 4, 6, 13, 15, 21, 23-HEXAENE (2)

CROSS-REFERENCES TO RELATED APPLICATIONS

This application claims priority to U.S. Provisional Patent Application 60/482,355, filed Jun. 25, 2003.

STATEMENT REGARDING FEDERALLY SPONSORED RESEARCH OR DEVELOPMENT

This invention was funded by a grant from the National Science Foundation No. DMR 9988881. The U.S. government has certain rights in this invention.

REFERENCE TO "COMPUTER LISTING APPENDIX SUBMITTED ON COMPACT DISC"

Not Applicable.

BACKGROUND OF THE INVENTION (1) Field of the Invention

The present invention relates to processes for the preparation of 1,4,7,10,13,16,21,24-OCTAAZABICYCLO[8.8.8] HEXACOSANE ($H_6$Aza222) (1) and 1,4,7,10,13,16,21,24-OCTAAZABICYCLO[8.8.8]HEXACOSA, 4,6,13,15,21, 23-HEXAENE (2). In a preferred process, the present invention relates to the preparation of compound (2) by reacting tris(2-aminoethyl) amine (tren), isopropyl alcohol (i-PrOH), and triethylamine ($Et_3N$) with cooling at a temperature below −30° C. Further, the present invention relates to the preparation of compound 1 from compound 2 by reacting an alkali metal and ammonia with compound 2 with cooling to a temperature below −30° C.

(2) Description of Related Art

Aza containing cryptands are known in the art and have a variety of uses as noted in U.S. Pat. No. 4,888,032 for instance. Such uses include, for instance, medical uses, water purification removing toxic heavy metals, binding metals as catalysts, electrides and alkalides. They are analogous to the non-aza cryptands of U.S. Pat. No. 4,257,955 to Gansow et al and U.S. Pat. No. 5,492,879 to Dye.

There is interest in nitrogen-donor cryptands for the preparation of room-temperature stable alkalides and electrides (Kim, J., et al., J. Am. Chem. Soc., 121 10666-10667 (1999)) which led to reinvestigation of the synthesis of 1,4,7,10,13, 16,21,24-octaazabicyclo[8.8.8]hexacosane (1), the aza analog of cryptand [2.2.2] (Xie, Q., et al., J. Am. Chem. Soc. 122 6971-6978 (2000)). Compound 1 was used for the preparation of the first barium sodide (Redko, M. Y., et al., JACS 125 2259-2263 (2003)). A reaction sequence in which tren is condensed with glyoxal to form the intermediate 1,4,7,10,13, 16,21,24-octaazabicyclo [8.8.8]hexacosa-4,6,13,15,21,23-hexaene (2) has been described by Smith et al (Smith, P. H., et al., J. Org. Chem. 58 7939-7941 (1993)), who also obtained the crystal structures of both compounds 1 and 2. While this method is satisfactory, it leads to gelatinous byproducts which lowered the yield and required the separation of compound 2 from the gelatinous byproducts via a 3-day Soxhlet extraction followed by filtration. The gels are polymers formed from the reactants and are very difficult to separate from the compound 2. The purified compound 2 was then reduced with $LiAlH_4$ in THF or $NaBH_4$ in MeOH to give a low overall purified yield of 45% of compound 1. A large excess of moderately expensive reducing agent(s) is required.

OBJECTS

It is therefore an object of the present invention to provide a significantly improved process for the preparation of compound (2) and then compound (1) from compound (2). These and other objects will become increasingly apparent from the following description and the drawings.

SUMMARY OF THE INVENTION

The present invention relates to a process for the preparation of 1,4,7,10,13,16,21,24-octaazabicyclo[8.8.8]hexacosa, 4,6,13,15,21,23-hexaene (2) which comprises: reacting a mixture of tris(2-aminoethyl)amine (tren) with glyoxal in the presence of water, a water miscible solvent and a tertiary amine with cooling to a temperature of about −30° C. or less, wherein the glyoxal is added slowly to the mixture, to prepare 1,4,7,10,13,16,21,24-octaazabicyclo [8.8.8]hexacosa, 4,6, 13,15,21,23-hexaene (2).

The present invention relates to a process for the preparation of 1,4,7,10,13,16,21,24-octaazabicyclo [8.8.8]hexacosa, 4,6,13,15,21,23-hexaene (2) which comprises: reacting a mixture of tris-2-aminoethyl)amine(tren), isopropyl alcohol (i-PrOH) and trialkylamine with glyoxal below −30° C., wherein the glyoxal is added slowly to the mixture, to prepare compound (2).

Preferably compound (2) is separated from the reaction mixture. Preferably the reaction mixture is heated to remove isopropyl alcohol thereby precipitating compound (2) which is separated from the reaction mixture. Preferably the precipitated and separated compound (2) is recrystallized in a solvent in the presence of a basic salt in water which removes byproducts. Preferably the cooling is with dry ice. Preferably the temperature is between −70° C. and −30° C.

The present invention also relates to a process for the preparation of 1,4,7,10,13,16,21,24-octaazabicyclo[8.8.8] hexacosane (1) which comprises: reacting in a non-reactive gas atmosphere a mixture of tris (2-aminoethyl)amine (tren) with glyoxal in the presence of water, a water miscible solvent and a tertiary amine with cooling to a temperature of about −30° C. or less, wherein the glyoxal is added slowly to the mixture, to prepare 1,4,7,10,13,16,21,24-octaazabicyclo [8.8.8]hexacosa, 4,6,13,15,21,23-hexaene (2); reacting compound (2) in a second mixture with an alkali metal in the presence of ammonia at a temperature of about −30° C. or less to form compound (1) from compound (2); causing the second mixture to warm to room temperature with removal of the ammonia; and separating compound (1) from the reaction mixture.

The present invention also relates to a process for the preparation of 1,4,7,10,13,16,21,24-octaazabicyclo[8.8.8]hexacosane (1) which comprises: reacting in a non-reactive gas atmosphere a mixture of tris(2-aminoethyl)amine (tren), isopropyl alcohol (i-PrOH) and triethylamine (Et$_3$N) with glyoxal with a first cooling of the mixture to between about −70° C. and −30° C., wherein the glyoxal is added slowly to the mixture, to prepare 1,4,7,10,13,16,21,24-octaazabicyclo[8.8.8]hexacosa, 4,6,13,15,21,23-hexaene (2); allowing the mixture including compound (2) to warm to room temperature; cooling the mixture including compound (2) with a second cooling; reacting compound (2) in a second mixture with an alkali metal in the presence of ammonia to form compound (1) from compound (2); allowing the second mixture to warm to room temperature with removal of the ammonia; and separating compound (1) from the reaction mixture.

Preferably compound (2) is separated by a non-polar, water immiscible organic solvent and water extraction so that compound (2) is in the organic solvent. Preferably the solvent is toluene or petroleum ether. Preferably the alkali metal is sodium. Preferably the cooling is with dry ice.

The present invention also relates to a process for the preparation of compound (1) which comprises: reacting compound (2) in a mixture of a lower alkanol containing 1 to 4 atoms with an alkali metal in the presence of ammonia with cooling of the mixture to a temperature of −30° C. or less to form compound (1) from compound (2); causing the mixture including compound (1) to warm with the removal of the ammonia; and separating compound (1) from the reaction mixture.

Finally the present invention relates to the process for the preparation of 1,4,7,10,13,16,21,24-octaazabicyclo[8.8.8]hexacosane (1) which comprises: reacting 1,4,7,10,13,16,21,24-octaazabicyclo[8.8.8]hexacosa,4,6,13,15,21,23-hexaene (2) in a mixture of isopropyl alcohol (i-PrOH) with an alkali metal in the presence of ammonia with cooling of the mixture to a temperature of −30° C. or less to form compound (1) from compound (2); allowing the mixture including compound (1) to warm to room temperature; and separating compound (1) from the reaction mixture.

Preferably compound (1) is separated by polar, water immiscible organic solvent-water extraction so that compound (1) is in the organic solvent. Preferably the solvent is toluene, isopropanol, petroleum ether, dichloromethane and mixtures thereof. Preferably the alkali metal is sodium. Preferably the cooling is with dry ice.

The literature process (Smith et al) for the synthesis of H$_6$Aza222 is:

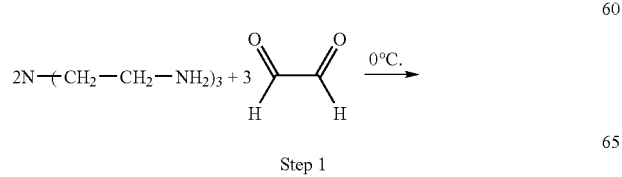

Step 1

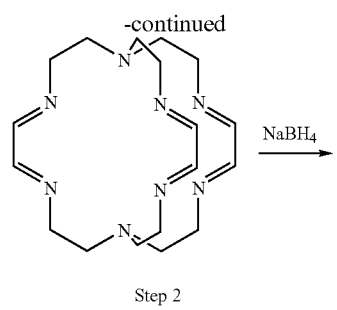

Step 2

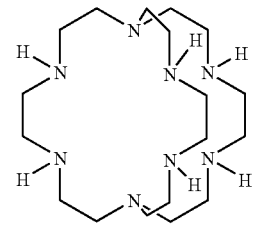

Step 1: This process takes time and a lot of effort to eliminate the gel. The process can not easily be scaled up. (52% yield and forms a lot of gel)
Step 2: Requires a large (25-fold) excess of reductant (NaBH$_4$) and solvent 85-86% yield. Total yield: ~45%
Productivity. ~1 g/2 weeks
The preferred process for synthesis of H$_6$Aza222 by the present invention is:

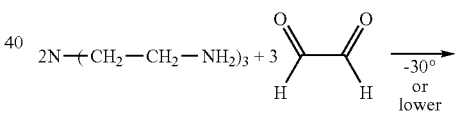

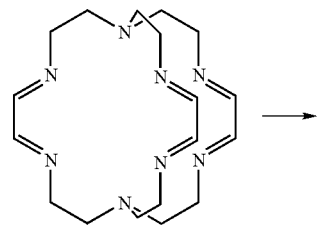

Step 1

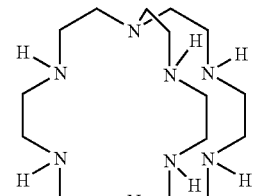

Step 2

Step 1:
>90% yield
Can avoid gel formation and it can be scaled up easily.

Step 2:
This reaction is performed in the same flask as step 1.
The process requires a small (<2-fold)excess of a cheap reductant.
Total yield: 65%
Productivity: ~20 g/3 days.

$H_6Aza222$ can be used by itself or be bound to a polymer:

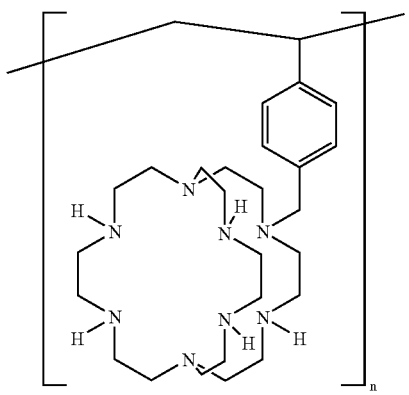

Such a polymer can strongly bind $Cd^{2+}$, $Hg^{2+}$, $Tl^{3+}$, $Pb^{2+}$.

Comparison of Aza222—based Polymer with Other Ion Exchange Polymers
1. Thio-based polymers oxidize on air:

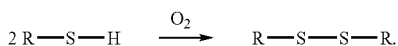

$H_6Aza222$ doesn't oxidize in air.

2. Polyamines form stable complexes with $CO^{2+}$, $Cu^{2+}$, $Ni^{2+}$, and $Zn^{2+}$, which are abundant elements. $H_6Aza222$ uses 8N atoms to bind $Cd^{2+}$ (and other heavy metals) and less nitrogen atoms to bind $Cu^{2+}$. This produces enhanced stability of the $H_6Aza222$-heavy metal complexes over $H_6Aza222$-$Cu^4$ which is an abundant element.

FIG. 2 shows the various uses for $H_6Aza222$. The uses are numerous.

DESCRIPTION OF PREFERRED EMBODIMENTS

Figure 1:
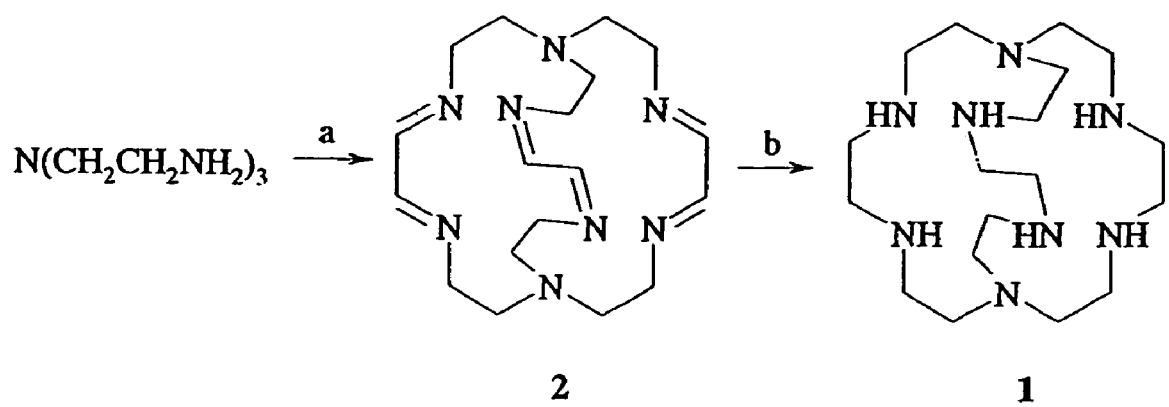
FIG. 1 is a drawing showing the reactions to produce compound 2 and then compound 1.
Figure 2:
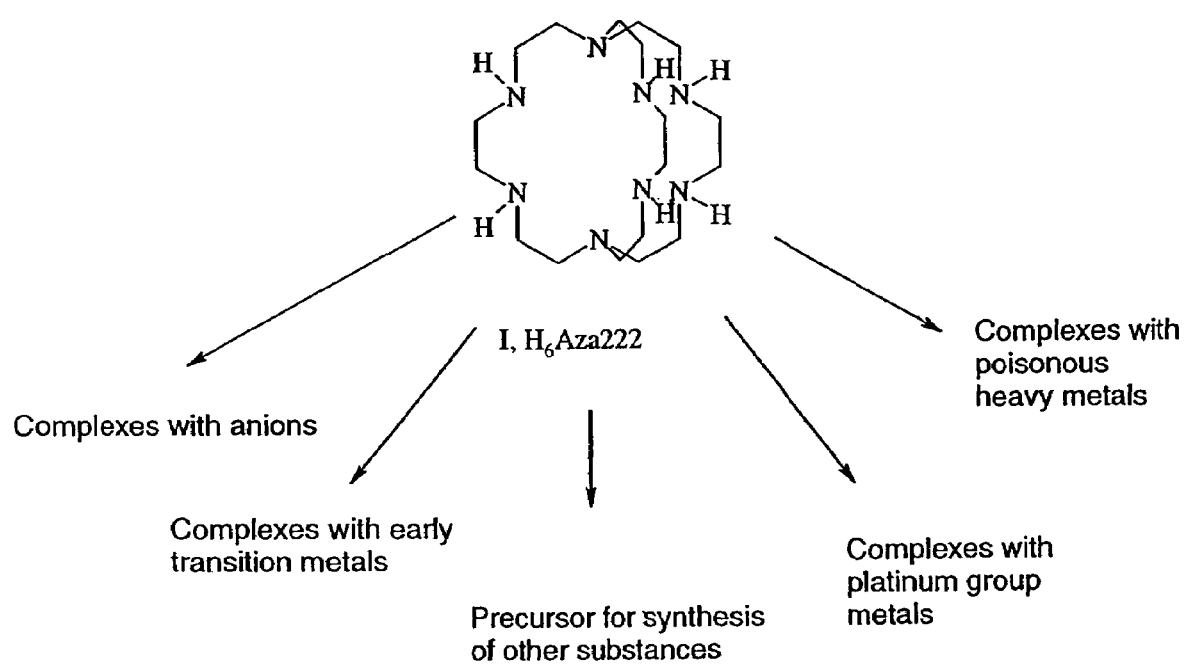
FIG. 2 is a chart showing various derivatives which can be prepared from the aza cryptand compound 1.

The peraza cryptand 1,4,7,10,13,16,21,24-octaazabicyclo [8.8.8]hexacosane (1) was made in a two-step one-pot procedure consisting of condensation of tris(2-aminoethyl)amine (tren) with glyoxal in isopropanol at −78° C. (dry ice) followed by the reduction of the intermediate with $Na$—$NH_3$ solution.

Preliminary attempts to condense tren with glyoxal at room temperature in the presence or absence of templating agents resulted in formation of white precipitates but no appreciable amounts of compound 2. The $^1H$ NMR spectra of these products exhibited two broad peaks centered around 2.6 ppm and 3.6 ppm, suggesting that amides of the type R—NH—$CH_2$—CONH—R had been formed via internal disproportionation, a known process (Chassonnery, D., et al., Bull. Soc. Chim. Fr., 131(2), 188 (1994); and Ferruti, P., et al., J. Chem. Soc. (C) 2512 (1970)). Based on the closely related reaction of N,N'-disubstituted ethylenediamines with glyoxal (Willer, R. L., et al., J. Org. Chem. 50 2368 (1985)), low temperatures and basic conditions should suppress such rearrangements (Bracco, S. P. A., International patent No WO 97/49691 (1997)).

The yield of compound 2 was increased to 91% by pre-cooling an isopropanol solution of tren to −78° C. before the addition of glyoxal and by adding triethylamine as a mild base. The solution of compound 2 so obtained could be easily filtered, with no need for Soxhlet extraction.

In order to achieve a one-pot synthesis, an isopropanol-compatible reduction of compound 2 to compound 1 was sought. In this solvent, $LiAlH_4$ would decompose, while $NaBH_4$ and $KBH_4$ are insufficiently soluble. Adding methanol or water to mixtures containing solutions of compound 2 and solid borohydrides resulted in partial reduction of compound 2 but most of the reducing agent decomposed by reaction with the solvent. Reaction of compound 2 with $BH_3$-THF complex in THF yielded a mixture with broad $^1H$ NMR peaks at 2.6 and 3.6 ppm, suggesting acid-catalyzed rearrangement. Direct reduction by alkali metals in isopropanol offered the requisite non-acidic conditions, simplicity, and ease of scale-up.

Initial experiments showed that Na/i-PrOH was not reactive enough to reduce compound 2 completely. Thus, a piece of Na remained in the solution even after one day of reaction at room temperature, leaving significant amounts of starting material. In addition to the reduction of compound 2, slow evolution of $H_2$ took place, indicating that proton transfer in the side reaction of Na with i-PrOH (and/or water) was competitive with electron transfer from Na to compound 2. Analysis of the reaction mixture by NMR showed that it contained both compound 1 and compound 2, but no intermediate reduction products were detected.

In a modification of that procedure, liquid NaK alloy was used for the reduction of compound 2 into compound 1, which has allowed compound 1 to be made with a yield of 25-30%. The extreme flammability of that alloy made us seek for other reducing agents and conditions. Thus, it was found that compound 2 could be reduced into compound 1 at 0° C. with Na in 1-butanol solution, which made the reduction step much safer. That modification, however, had its own drawbacks: the reduction reaction took two days instead of one, and, later, it was more difficult to get rid of 1-butanol than isopropanol because of the higher boiling point of the former solvent.

Whenever the reduction was performed at or around 0° C., the yield of compound 1 did not exceed 35% and the rest of the reaction products consisted of tren, other amines and their unidentified derivatives. Since the formation of compound 2 from tren and glyoxal was virtually quantitative and no tren or other amines were detected in the reaction mixture obtained after addition of glyoxal to tren, it was thought that those byproducts were generated in side reactions of compound 2 with strong bases.

It was unexpectedly found that an ideal reductant for compound 2 was a liquid Na—$NH_3$ solution at −78° C. because of the following reasons:

1) The rate constants of electron transfer processes were high;

2) The area of contact of two liquid phases (alcohol, containing compound 2, and Na—$NH_3$ solution) was made high by stirring the reaction mixture;

3) The other reactions were suppressed by the low temperature.

It was unclear, though, whether compound 2 would react with $NH_3$ and whether water, dissolved in alcohol, would react with Na—$NH_3$ solution slowly enough. To test the stability of compound 2 in presence of $NH_3$, a 100 mg sample of solid compound 2 was dissolved in 1 ml of i-PrOH at room temperature, then 0.5 ml $NH_3$ were condensed onto that solution, and the obtained mixture was allowed to stand for 12 hrs at room temperature. After that the solvents were removed under vacuum, and the analysis of the resulting solid revealed that it was an unchanged compound 2. The followed experiment where compound 2 was reduced with Na—$NH_3$ solution indeed resulted in a formation of compound 1 in a course of a fast reaction and gave much higher yield of compound 1 than the other reducing systems. The rate of reaction of Na with $H_2O$, present in the reaction mixture, was virtually negligible.

An experiment was performed where compound (2) was made by simultaneous addition of tren and glyoxal to isopropanol in presence of an amine other than triethylamine is given in Example 3. Because amounts of the reactants that were added to a cold isopropanol simultaneously were large, the reaction mixture solidifies after reduction with sodium, which indicates that larger amounts of compound 1 could not be made without increasing the volume of the reaction flask.

Another feature of the last synthesis was formation of a significant amount of gel in a solution. That phenomenon complicated the syntheses. Two things were done to simplify the work with those solutions:

1) Hexane was added to the isopropanol solution, containing the gel, which resulted in precipitation of most of the gel; and 2) The isopropanol-hexane solution, containing compound (1) and a very small amount of gel, was filtered through Celite-300. Usually, even a small amount of gel suffice to jam the filter. However, it was found that gel was highly soluble in water. Thus, whenever the rate of filtration decreased, water was added to isopropanol-hexane mixture, which resulted in gel dissolution, which greatly increased the rate of filtration.

In summary, a relatively large scale, two-day, one-pot synthesis of compound 1 from commercially available reactants has been developed (FIG. 1). This method avoids the formation of gelatinous by-products, eliminating the need to isolate and purify compound 2, and is easily scaled up for the production of compound 1. The overall yield was improved over previous literature reports, the procedure represents a significant simplification in the preparation of this polyamine macrocycle, and we anticipate that the general approach outlined herein should apply broadly to similar synthetic targets.

EXAMPLES

General

All solid and liquid reagents were purchased from Aldrich Chemical Co. (Milwaukee, Wis.) and were used as received. Compressed $NH_3$ was purchased from Matheson. All the reactions were performed in dry $N_2$ atmosphere. NMR $^1H$ and $^{13}C$ spectra were recorded on a Varian Gemini 300 Spectrometer. GC-MS analyses were run on a HP 5890, series II Gas Chromatograph, coupled with a VG-Trio-1 mass spectrometer. CHN elemental analysis was done in a Perkin Elmer CHNS/O Analyzer 2400 Series II.

Example 1

Synthesis of Compound 2

A mixture of 9.73 g (66.6 mmoles) of 96% tren, 25 mL of 99.5% $Et_3N$ and 500 mL of 99% i-PrOH was prepared in a 1 L 3-neck round-bottom flask equipped with an addition funnel and mechanical stirrer and the resulting solution was cooled to −78° C. with a dry ice-isopropanol bath. Initial concentration of tren =0.127 M. A solution of 14.50 g 40% aqueous glyoxal (0.100 mole), diluted to 250 mL with isopropanol, was then added at a rate of 2 drops/sec with vigorous stirring. (Initial concentration of glyoxal=0.40M.)

After addition was complete, the ice bath was removed and the reaction mixture was allowed to warm up to room temperature. Solvent was removed on a rotary evaporator at 40° C., yielding 13.5 g of yellow-brown crystalline solid, which was redissolved in $CHCl_3$. This solution was filtered through sand to remove the small amount of gel that had formed. When the solvent was removed this yielded 10.88 g (91%) of compound 2 which appeared pure by $^1H$ and $^{13}C$ NMR. Since compound 2 formed more gel upon contact with chloroform, either in bulk or in the NMR tube, no further attempts were made at recrystallization of compound 2 from $CHCl_3$. $^1H$ NMR: 2.692 (br, 12H), 3.512 (br, 12H), 7.693 ppm (s, 6H). $^{13}C$ NMR: 52.864, 58.996, 162.942 ppm; MS: m/e 358 ($M^+$).

Later it was found that crude compound 2 could also be purified by dissolution in hot acetonitrile in contact with saturated aqueous $K_2CO_3$. The colored and/or gel-forming substances go into the aqueous phase, and colorless crystals of compound 2 form upon cooling of the separated acetonitrile solution.

Example 2

Synthesis of Compound 1

20.3 g (0.14 moles) of 96% tren, 25 mL of 99.5% $Et_3N$ and 1 L of 99% i-PrOH were put into a 2 L 3-neck round-bottom flask equipped with mechanical stirrer and dry nitrogen inlet and cooled to −78° C. in a dry ice-isopropanol bath. Initial concentration of tren=0.110 M. To this mixture, a solution of 30.5 g 40% aqueous glyoxal (0.21 moles), diluted to 250 mL with isopropanol, was added with vigorous stirring over 6 hr in a nitrogen atmosphere. Initial concentration of glyoxal=0.84 M. Then the reaction mixture was allowed to warm up overnight to ensure that the formation of compound 2 was complete.

On the next day the solution was cooled down to −78° C. again and sodium metal (49 g, 2.13 mole), cut into 1 g pieces, was added to the solution upon gentle stirring. After that gaseous $NH_3$ was blown into the solution till the volume of the liquid increased by ~500 mL. By that time small drops of Na—$NH_3$ golden liquid phase, surrounded by thin blue diffusion layers, started to float to the surface. The ammonia addition was then stopped, the solution was vigorously stirred for 10 minutes and then it was allowed to warm up to room temperature overnight.

By the time the reaction mixture warmed up to room temperature, ammonia was virtually gone and no Na metal was left. The obtained white slurry was poured into 2 L separation funnel, 300 mL toluene and 200 ml $H_2O$ were added to it, the whole flask was stirred and allowed to stand for an hour. When the phases separated, the lower phase, containing concentrated solution of NaOH, was separated, the rest of the solution was evaporated under vacuum at 100° C., and, when the resulting viscous liquid was allowed to cool down to room temperature, it yielded solid impure compound 1. That compound 1 was recrystallized from 100 mL $H_2O$ to give 20.0 g $H_6Aza222*4H_2O$ that was filtered at 0° C. and dried on filter. The composition of the hydrate was deduced from the results of CHN analyses. Yield of 1*$4H_2O$: 20.0 g (64.5%). $^1H$ NMR ($CDCl_3$ containing $D_2O$): 2.477 ppm (t, J=5.4 Hz, 12H), 2.722 ppm (t, J=5.4 Hz, 12H) and 2.753 ppm (s, 12H). $^{13}C$ NMR ($CDCl_3$): 46.237, 49.196 and 50.866 ppm. MS:m/e 371.4 $(M+1)^+$. CHN:48.20% C, 11.24% H, 24.80% N. Calc. For 1*$4H_2O$: 48.84% C, 25.31% N, 11.39% H.

Example 3

Synthesis of Compound 1

A 2 L 3-neck round-bottom flask equipped with a mechanical stirrer was charged with 50 mL of 98% tripropylamine and 1 L of 99% i-PrOH, and cooled to −78° C. in a dry ice-isopropanol bath. To this mixture, solutions of 45.0 g 40% aqueous glyoxal (0.310 mole), diluted to 250 mL with isopropanol, and 30.0 g (0.205 moles) of 96% tren, diluted to 250 mL, were simultaneously added over a period of 2 hrs with vigorous stirring. (Initial concentration of glyoxal=1.24 M; Initial concentration of tren=0.82 M). Then the reaction mixture was allowed to warm up overnight and briefly warmed up to 60° C. to ensure that the formation of compound 2 was complete. It was cooled to room temperature while nitrogen gas was blown over its surface.

On the next day the remaining solution (its volume had decreased to ~500 mL as a result of a partial solvent evaporation) was cooled down to −78° C. Sodium metal (49 g, 2.13 mole), cut into six roughly equal pieces, was added to the solution with gentle stirring in a nitrogen atmosphere. Gaseous $NH_3$ was then bubbled into the solution until the volume of the liquid increased by ~500 mL. At this point, small drops of Na—$NH_3$ golden liquid phase, surrounded by thin blue diffusion layers, started to float to the surface. The ammonia addition was then stopped and the solution was allowed to warm up to room temperature for 24 hrs with gentle stirring.

By the time the reaction mixture warmed up to room temperature, the flask was filled with semisolid reaction products, mostly sodium isopropoxide, sodium hydroxide, sodium metal, compound 1 and geleous byproducts. The ammonia was virtually gone. Fresh isopropanol (100 ml) and 200 ml of water were added to the reaction mixture and the mixture was refluxed, which resulted in dissolution of the remaining sodium metal and formation of two liquid layers. The top layer consisted mostly of isopropanol and contained virtually all of compound 1, with suspended geleous particles. The bottom layer consisted mostly of saturated sodium hydroxide solution. Hexane (200 mL) was added to the reaction mixture, which lead to precipitation of virtually all of the gel from the top layer.

The top phase was filtered through a layer of Celite-300. If necessary, any gel blocking the Celite was dissolved in water. The resultant solution was evaporated, the viscous semisolid material dissolved in 250 ml of hot water, and, when water cooled to 0° C., compound 1 crystallized as a hydrate. The solid hydrate of compound 1 was filtered, rinsed with a minimal amount of cold water, and dried under vacuo. Yield of anhydrous compound 1 was 22.65 g (61% from theoretical).

It is intended that the foregoing description be only illustrative of the present invention and that the present invention be limited only by the hereinafter appended claims.

We claim:
1. A process for the preparation of 1,4,7,10,13,16,21,24-octaazabicyclo[8.8.8]hexacosa-4,6,13,15,21,23-hexaene (2) which comprises:
   (a) reacting a mixture of tris(2-aminoethyl)amine (tren) with glyoxal in the presence of water, a water miscible solvent and a tertiary amine with cooling to a temperature of about −30° C. or less, wherein the glyoxal is added slowly to the mixture, to prepare 1,4,7,10,13,16,21,24-octaazabicyclo[8.8.8]hexacosa-4,6,13,15,21,23-hexaene (2) without formation of gelatinous byproducts.
2. The process of claim 1 wherein 1,4,7,10,13,16,21,24-octaazabicyclo[8.8.8]hexacosa-4,6,13,15,21,23-hexaene (2) is separated from the reaction mixture.
3. The process in claim 1 wherein the reaction mixture is heated to remove the solvent thereby precipitating 1,4,7,10,13,16,21,24-octaazabicyclo[8.8.8]hexacosa-4,6,13,15,21,23-hexaene (2) which is separated from the reaction mixture.
4. The process of claim 3 wherein the precipitated and separated 1,4,7,10,13,16,21,24-octaazabicyclo[8.8.8]hexacosa-4,6,13,15,21,23-hexaene (2) is recrystallized from an organic solvent in the presence of a basic salt in water that dissolves any of the byproducts.
5. The process of any one of claims 1, 2, 3 or 4 wherein the cooling is with dry ice.
6. A process for the preparation of 1,4,7,10,13,16,21,24-octaazabicyclo[8.8.8]hexacosane (1) which comprises:
   (a) reacting in a non-reactive gas atmosphere a mixture of tris(2-aminoethyl)amine (tren) with glyoxal in the presence of water, a water miscible solvent and a tertiary amine with cooling to a temperature of about −30° C. or less, wherein the glyoxal is added slowly to the mixture, to prepare 1,4,7,10,13,16,21,24-octaazabicyclo[8.8.8]hexacosa-4,6,13,15,21,23-hexaene (2) without formation of gelatinous byproducts;
   (b) reacting compound (2) in the mixture of step (a) with an alkali metal, in isopropanol in the presence of ammonia at a temperature of about −30° C. or less to form compound (1) from compound (2);
   (c) causing the second mixture to warm to room temperature with removal of the ammonia; and
   (d) separating compound (1) from the reaction mixture into an organic solvent for compound (1).

7. The process of claim 6 wherein 1,4,7,10,13,16,21,24-octaazabicyclo[8.8.8]hexacosane (1) is separated in step (d) by the organic solvent and water extraction so that 1,4,7,10,13,16,21,24-octaazabicyclo[8.8.8]hexacosane (1) is in the organic solvent.

8. The process of claim 7 wherein the organic solvent is selected from the group consisting of toluene, isopropanol, petroleum ether, dichloromethane and mixtures thereof.

9. The process claim 6 wherein the alkali metal is sodium.

10. The process of any one of claims 6, 7, 8 or 9 wherein the cooling is with dry ice.

11. A process for the preparation of 1,4,7,10,13,16,21,24-octaazabicyclo[8.8.8]hexacosane (1) which comprises:
   (a) reacting 1,4,7,10,13,16,21,24-octaazabicyclo[8.8.8]hexacosa-4,6,13,15,21,23-hexaene (2) in a mixture of a lower alkanol containing 1 to 4 atoms with an alkali metal in the presence of ammonia with cooling of the mixture to a temperature of $-30°$ C. or less to form compound (1) from compound (2);
   (b) causing the mixture including compound (1) to warm with the removal of the ammonia; and
   (c) separating compound (1) from the reaction mixture.

12. The process of claim 11 wherein 1,4,7,10,13,16,21,24-octaazabicyclo[8.8.8]hexacosane (1) is separated by an organic solvent-water extraction so that compound (1) is in the organic solvent, and wherein the solvent is selected from the group consisting of toluene, petroleum ether, isopropanol, dichloromethane and mixtures thereof.

13. The process of claim 11 wherein the alkali metal is sodium.

14. The process of claim 11 wherein the cooling is with dry ice.

15. A process for the preparation of 1,4,7,10,13,16,21,24-octaazabicyclo[8.8.8]hexacosa-4,6,13,15,21,23-hexaene (2) which comprises:
   (a) reacting a mixture of tris(2-aminoethyl)amine (tren) with glyoxal in the presence of water, isopropyl alcohol (i-PrOH) and triethylamine ($Et_3N$) with cooling to a temperature of about $-30°$ C. or less, wherein the glyoxal is added slowly to the mixture, to prepare 1,4,7,10,13,16,21,24-octaazabicyclo[8.8.8]hexacosa-4,6,13,15,21,23-hexaene (2) without formation of gelatinous byproducts.

16. The process of claim 15 wherein 1,4,7,10,13,16,21,24-octaazabicyclo[8.8.8]hexacosa-4,6,13,15,21,23-hexaene (2) is separated from the reaction mixture.

17. The process in claim 15 wherein the reaction mixture is heated to remove isopropyl alcohol (i-PrOH) thereby precipitating 1,4,7,10,13,16,21,24-octaazabicyclo[8.8.8]hexacosa-4,6,13,15,21,23-hexaene (2) which is separated from the reaction mixture.

18. The process of claim 17 wherein the precipitated and separated 1,4,7,10,13,16,21,24-octaazabicyclo[8.8.8]hexacosa-4,6,13,15,21,23-hexaene (2) is recrystallized from an organic solvent in the presence of a basic salt in water that dissolves byproducts.

19. The process of any one of claims 15, 16, 17 or 18 wherein the cooling is with dry ice.

20. A process for the preparation of 1,4,7,10,13,16,21,24-octaazabicyclo[8.8.8]hexacosane (1) which comprises:
   (a) reacting in a non-reactive gas atmosphere a mixture of tris(2-aminoethyl)amine (tren) with glyoxal in the presence of water, isopropyl alcohol (i-PrOH) and triethylamine ($Et_3N$) with cooling to a temperature of about $-30°$ C. or less, wherein the glyoxal is added slowly to the mixture, to prepare 1,4,7,10,13,16,21,24-octaazabicyclo[8.8.8]hexacosa-4,6,13,15,21,23-hexaene (2) without formation of gelatinous byproducts;
   (b) reacting compound (2) in a second mixture with an alkali metal in the presence of ammonia at a temperature of about $-30°$ C. or less to form compound (1) from compound (2);
   (c) causing the second mixture to warm to room temperature with removal of the ammonia; and
   (d) separating compound (1) from the reaction mixture.

21. The process of claim 20 wherein 1,4,7,10,13,16,21,24-octaazabicyclo[8.8.8]hexacosane (1) is separated in step (d) by an organic solvent and water extraction, so that 1,4,7,10,13,16,21,24-octaazabicyclo[8.8.8]hexacosane (1) is in the organic solvent.

22. The process of claim 21 wherein the organic solvent is selected from the group consisting of toluene, petroleum ether, isopropanol, dichloromethane and mixtures thereof.

23. The process claim 20 wherein the alkali metal is sodium.

24. The process of any one of claims 20, 21, 22, or 23 wherein the cooling is with dry ice.

25. A process for the preparation of 1,4,7,10,13,16,21,24-octaazabicyclo[8.8.8]hexacosane (1) which comprises:
   (a) reacting 1,4,7,10,13,16,21,24-octaazabicyclo[8.8.8]hexacosa-4,6,13,15,21,23-hexaene (2) in a mixture of isopropyl alcohol (i-PrOH) with an alkali metal in the presence of ammonia with cooling of the mixture to a temperature of $-30°$ C. or less to form compound (1) from compound (2);
   (b) causing the mixture including compound (1) to warm with the removal of the ammonia; and
   (c) separating compound (1) from the reaction mixture.

26. The process of claim 25 wherein 1,4,7,10,13,16,21,24-octaazabicyclo[8.8.8]hexacosane (1) is separated by an organic solvent-water extraction so that 1,4,7,10,13,16,21,24-octaazabicyclo[8.8.8]hexacosane (1) is in the organic solvent, and wherein the solvent is selected from the group consisting of toluene, petroleum ether, isopropanol or dichloromethane and mixtures thereof.

27. The process of claim 25 wherein the alkali metal is sodium.

28. The process of claim 25 wherein the cooling is with dry ice.

29. The process of claim 1 wherein the water miscible solvent is isopropanol.

30. The process of claim 6 wherein the water miscible solvent in step (a) is isopropanol.

31. The process of claim 6 wherein the water miscible solvent in step (a) is isopropanol and the alkali metal in step (b) is sodium metal.

* * * * *